US009445938B1

(12) United States Patent
Wagner

(10) Patent No.: US 9,445,938 B1
(45) Date of Patent: *Sep. 20, 2016

(54) ORAL DEVICES

(71) Applicant: Wayne R. Wagner, The Woodlands, TX (US)

(72) Inventor: Wayne R. Wagner, The Woodlands, TX (US)

(73) Assignee: W.R. WAGNER FAMILY LIMITED PARTNERSHIP, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/005,116

(22) Filed: Jan. 25, 2016

Related U.S. Application Data

(63) Continuation of application No. 14/189,772, filed on Feb. 25, 2014, now Pat. No. 9,408,743, which is a continuation-in-part of application No. 13/456,682, filed on Apr. 26, 2012, now Pat. No. 9,144,512.

(51) Int. Cl.
*A61F 5/56* (2006.01)

(52) U.S. Cl.
CPC ..................... *A61F 5/566* (2013.01)

(58) Field of Classification Search
CPC ............... A63B 2071/086; A63B 2208/12; A63B 71/085; A63B 2071/088; A61F 5/58; A61F 5/56; A61F 5/566; A61F 5/50; A61B 13/00; A61C 5/14
See application file for complete search history.

(56) References Cited

U.S. PATENT DOCUMENTS

| 3,132,647 A | 5/1964 | Corniello |
| 3,434,470 A | 3/1969 | Strickland |
| 4,304,227 A | 12/1981 | Samelson |
| 4,396,373 A | 8/1983 | Dellinger |
| 4,531,916 A | 7/1985 | Scantlebury et al. |
| 4,671,767 A | 6/1987 | Blechman et al. |

(Continued)

FOREIGN PATENT DOCUMENTS

| EP | 1205157 A1 | 5/2002 |
| EP | 1203570 B1 | 11/2011 |

(Continued)

OTHER PUBLICATIONS

Bailey, Premarket Notification [510(k)] Summary K013049 for mandibular repositioning appliance (device) known as NOrAD(TM), clearance granted by United States FDA, Nov. 29, 2001.

(Continued)

*Primary Examiner* — Ophelia A Hawthorne
(74) *Attorney, Agent, or Firm* — Jeffrey L. Wendt; The Wendt Firm, P.C.

(57) ABSTRACT

Apparatus for reducing obstructive sleep apnea, snoring and/or nasal drainage. One apparatus includes an upper member fitting the interior and exterior surfaces of a user's upper dentition, and a lower member fitting similarly adjacent a user's lower dentition. The lower member includes eyeteeth extensions projecting away from the lower member. The upper member includes molar extensions projecting away from the upper member and toward the member molar regions so that when the user bites or clenches, the upper right and lower right extensions impinge on one another in substantially overlapping fashion, as do the upper left and lower left extensions. The upper and lower members have an anterior shape to form a gap sufficient for the user's tongue to extend into the gap, and each molar extension may include a magnet. Methods of using the apparatus and kits to reduce sleep apnea, snoring, and/or nasal drainage.

4 Claims, 3 Drawing Sheets

(56) References Cited

U.S. PATENT DOCUMENTS

| | | |
|---|---|---|
| 4,676,240 A | 6/1987 | Gardy |
| 4,700,697 A | 10/1987 | Mundell et al. |
| 4,708,646 A | 11/1987 | Jasper |
| 4,715,368 A | 12/1987 | George |
| 4,901,737 A | 2/1990 | Toone |
| 5,013,243 A | 5/1991 | Tanaka et al. |
| 5,056,534 A | 10/1991 | Wright |
| 5,117,816 A | 6/1992 | Shapiro et al. |
| 5,239,995 A | 8/1993 | Estes et al. |
| 5,499,633 A | 3/1996 | Fenton |
| RE35,295 E | 7/1996 | Estes et al. |
| 5,570,704 A | 11/1996 | Buzzard et al. |
| 5,611,355 A | 3/1997 | Hilsen |
| 5,678,998 A | 10/1997 | Honkura et al. |
| 5,683,244 A | 11/1997 | Truax |
| 5,692,521 A | 12/1997 | Leasure-Nelson |
| 6,074,207 A | 6/2000 | Coats |
| 6,082,363 A | 7/2000 | Washburn |
| 6,109,265 A | 8/2000 | Frantz et al. |
| 6,213,959 B1 | 4/2001 | Kushida |
| 6,299,450 B1 | 10/2001 | Honkura et al. |
| 6,427,689 B1 | 8/2002 | Estes |
| 6,491,037 B1 | 12/2002 | Mortenson |
| 6,505,625 B1 | 1/2003 | Uenishi |
| 6,659,771 B2 | 12/2003 | Honkura et al. |
| 6,766,802 B1 | 7/2004 | Keropian |
| 7,107,992 B2 | 9/2006 | Brooks et al. |
| 7,178,529 B2 | 2/2007 | Kownacki |
| 7,225,021 B1 | 5/2007 | Park et al. |
| 7,255,110 B2 | 8/2007 | Knudson et al. |
| 7,322,356 B2 | 1/2008 | Critzer et al. |
| 7,451,767 B2 | 11/2008 | Keropian |
| 7,540,843 B2 | 6/2009 | De Backer |
| 7,607,439 B2 | 10/2009 | Li |
| 7,637,262 B2 | 12/2009 | Bailey |
| 7,712,468 B2 | 5/2010 | Hargadon |
| 7,810,502 B1 | 10/2010 | Nguyen et al. |
| 8,215,312 B2 | 7/2012 | Garabadian et al. |
| 9,144,512 B2 * | 9/2015 | Wagner .................. A61C 7/006 |
| 2001/0027793 A1 | 10/2001 | Tielmans |
| 2004/0177852 A1 | 9/2004 | Abramson |
| 2005/0121039 A1 | 6/2005 | Brooks et al. |
| 2005/0236003 A1 | 10/2005 | Meader |
| 2006/0252685 A1 | 11/2006 | Gould |
| 2006/0289013 A1 | 12/2006 | Keropian |
| 2007/0283967 A1 | 12/2007 | Bailey |
| 2008/0060660 A1 | 3/2008 | Nelson et al. |
| 2008/0173312 A1 | 7/2008 | Peake et al. |
| 2008/0199824 A1 | 8/2008 | Hargadon |
| 2008/0210244 A1 | 9/2008 | Keropian |
| 2008/0257358 A1 | 10/2008 | Stern et al. |
| 2008/0264422 A1 | 10/2008 | Fishman |
| 2008/0276938 A1 | 11/2008 | Jeppeson et al. |
| 2009/0036889 A1 | 2/2009 | Callender |
| 2009/0056724 A1 | 3/2009 | Keropian |
| 2009/0120448 A1 | 5/2009 | Keropian |
| 2009/0188510 A1 | 7/2009 | Palmer |
| 2010/0211184 A1 | 8/2010 | Rousseau et al. |
| 2010/0224197 A1 | 9/2010 | Keropian |
| 2010/0300458 A1 | 12/2010 | Stubbs et al. |

FOREIGN PATENT DOCUMENTS

| | | |
|---|---|---|
| WO | WO 2007/134375 | 11/2007 |
| WO | WO 2010/040026 | 4/2010 |
| WO | WO 2010/062952 | 6/2010 |
| WO | WO 2010/093264 | 8/2010 |

OTHER PUBLICATIONS

Bailey, Premarket Notification [510(k)] Summary K020893 for mandibular repositioning appliance (device) known as NOrAD(TM), clearance granted by United States FDA, May 28, 2002.

Britishsnoring; Tomed SomnoGuard FittingHeated for 20 seconds, YouTube video, uploaded to the Internet by britishsnoring on Apr. 26, 2010, http://www.youtube.com/watch?v=OXfN76M2I1A.

Department of Health & Human Services; K964516; Letter to James Bonds of Nellcor Puritan Bennett, Incorporated; Jun. 2, 2005; Rockville, MD; US.

Dynasplint; Wearing your Jaw Dynasplint® System, YouTube video, uploaded to the Internet by dynasplint on Oct. 5, 2011, http://www.youtube.com/watch?v=3hjP24aByd4.

European Patent Office; "Invitation to Pay Additional Fees and, Where Applicable, Protest Fee" for PCT/US2012/036474; Jul. 25, 2012; Rijswijk; Netherlands.

European Patent Office; International Search Report for PCT/US2012/036474; 6 pages, Sep. 9, 2012; Rijswijk, Netherlands.

European Patent Offoce; Written Opinion of the International Searching Authority for PCT/US2012/036474, 12 pages, Sep. 9, 2012; Munich, Germany.

FDA 510(k) Summary K033822, Feb. 6, 2004.

FDA 510(k) Summary K033823, Feb. 6, 2004.

FDA 510(k) Summary K042161, Oct. 27, 2004.

FDA 510(k) Summary K061688, Sep. 8, 2006.

FDA 510(k) Summary K102118, Sep. 8, 2010; Ranir, LLC, 510(k) Summary K102118 for Intraoral Anti-Snoring Device known as Snore Guard Advance(TM), clearance granted by United States FDA, Sep. 8, 2010.

FDA 510(k) Summary K121761, Sep. 28, 2012.

FDA 510(k) Summary K962516, Sep. 10, 1996.

FDA 510(k) Summary K972061, Aug. 21, 2007; Thornton; Non-Confidential Summary of Safety and Effectiveness; K972061; Aug. 21, 1997; Dallas, TX; US.

FDA 510(k) Summary; Wagner Direct; FDA 501K Summary; Apr. 15, 2014; Houston, Texas; US.

Hoffstein; "Review of oral appliances for treatment of sleep-disordered breathing", Sleep Breath (2007) 11 :1-22, published online Nov. 29, 2006, Springer-Verlag; Germany.

Houston-Chronicle; "Tired of Your CPAP?", Jan. 16, 2011.

I Hate Crap!; "Sleep Apnea Appliances, I Hate CPAP!", p, 1-8, downloaded from the Internet Oct. 25, 2010; http://www.ihatecpap.com/oral_appliances.html'; Illinois; US.

Landers, SJ, "Link strengthened between sleep apnea and mortality risk", amednews, Sep. 1, 2008; American Medical Association; US.

Pancer, et al., "Evaluation of Variable Mandibular Advancement Appliance for Treatment of Snoring and Sleep Apnea", Chest (1999); 116:1511-1518; Clinical Investigations; US.

Prehn, Ronald S" "What is a Mandibular Advancement Splint and How Does it Work?", YouTube video, uploaded to the Internet by rsprehn on Mar. 4, 2010, http://www.youtube.com/watch?v=OWiQQF4xQZc.

Randerath et al., "Non-CPAP therapies in obstructive sleep apnoea", Eur Respir J (no month, 2011); vol. 37, No. 5; pp. 1000-1028; Paris, France.

Sybron Dental Specialties; 510(k) Summary K070327 for Intraoral Devices for Snoring and Intraoral Devices for Snoring and Obstructive Sleep Apnea known as Removable Acrylic Herbst(TM), Allesee Snore Appliance(TM), and Enoch Snorinator(TM), clearance granted by United States FDA, May 25, 2007; Sturtevant, WI; US.

* cited by examiner

ORAL DEVICES

CROSS-REFERENCE TO RELATED APPLICATIONS

This application is a continuation of U.S. application Ser. No. 14/189,772, filed Feb. 25, 2014, which was a continuation-in-part of U.S. application Ser. No. 13/456,682, filed Apr. 26, 2012, now U.S. Pat. No. 9,144,512, both of which are incorporated herein by reference in their entirety.

BACKGROUND INFORMATION

1. Technical Field

The present disclosure relates to oral devices for reducing or eliminating obstructive sleep apnea, snoring and/or nasal drainage.

2. Background Art

Sleep apnea is a reduction in the blood oxygen level due to any cause. The present disclosure relates to "obstructive sleep apnea", which is problematic for many people—about 12 to 18 million people in the United States as of 2008. Obstructive sleep apnea (OSA) involves a reduction in breathing, called hypopneas, or a complete halt in airflow, called apneas, during sleep. Most pauses last 10 to 30 seconds, but some may persist for one minute or longer, according to the American Academy of Sleep Medicine. See Landers, S J, "*Link strengthened between sleep apnea and mortality risk*", amednews, Sep. 1, 2008. As indicated in this article, apnea has been linked to higher mortality risks.

There are of course many known devices which claim to reduce or eliminate OSA, and these devices typically fall in two categories: external masks, such as the CPAP (continuous positive airway pressure) masks; and oral devices, sometimes referred to as mandibular splints. Pharmaceuticals comprise another category. The present disclosure involves the oral device or mandibular splint category.

Another discomfort is nasal or sinus drainage, sometimes referred to as nasal or sinus congestion, nasal or sinus drip, nasal or sinus irritation. The term "nasal drainage" is used herein to include all of these conditions unless otherwise noted. Non-oral products, such as adhesive strips positioned on the nose, may relieve some of these symptoms. However, nasal strips may only reduce anterior (frontal) congestion, and not posterior (throat) congestion.

Many of the known oral devices are uncomfortable and/or complicated, leading to reduced use. Furthermore, their use in humans may reduce speaking substantially, or at least the ability to speak understandably. In my co-pending application Ser. No. 13/456,682, filed Apr. 26, 2012, now issued as U.S. Pat. No. 9,144,512, incorporated herein by reference, certain embodiments include left and right ramps designed to move the lower mandible (lower jaw) downward as it moves backward toward a users throat. While I have found devices of this nature to be effective in reducing or eliminating my sleep apnea and snoring, and met a long felt and unmet need for an oral device, apparatus or kit, and methods of using these, to efficiently, safely and comfortably reduce or prevent OSA, snoring, and/or nasal drainage, the shape of the ramps may be complicated to manufacture. In particular, the ramps disclosed in my previous patent application each have complicated mating surfaces. Considering FIG. 8 of my '512 patent, specifically the right ramp, the right ramp may be described as being defined by three upper right surfaces or faces, with smooth transitions from face to face, and three mating lower right surfaces or faces, that interface and that must move smoothly against each other at any given time: a flat front, generally horizontal face, a generally slanted face, and a generally flat rear, generally horizontal face. The same may be said of the left ramp. Therefore, each side has three interfaces, for a total of six interfaces for the device, which must move smoothly to be comfortable and effective for users.

Another device, disclosed in WO20100093264A1, is designed for use in medical procedures to repair damaged facial features. The devices include left and right forward inclined ramps on the lower tray of the device. Ramps of suitable height could alternately be positioned on the upper tray only, or on both trays. However, this device also includes engagement features to engage posterior portions of upper and lower trays to stabilize the upper and lower trays relative to one another, and thereby stabilize the subject's upper and lower jaw relative to one another, in contrast to the goal of the present devices. Such stabilization in devices designed to prevent snoring and/or sleep apnea are highly undesirable, as they lead to jaw soreness and stiffness, and ultimately lead to non-use.

I have now designed an oral device that reduces possible alignment problems with my previous device and devices of like nature, and which is easier to manufacture.

SUMMARY

In accordance with the present disclosure, oral devices, apparatus and kits are presented, as well as methods of using same, which reduce or overcome one or more of the problems of obstructive sleep apnea, snoring and other loss of sleep issues, and/or nasal drainage.

A first aspect of the disclosure is an apparatus (the words "apparatus" and "oral device" are used interchangeably herein) comprising:

upper and lower generally arched-shaped members configured to fit adjacent at least a portion of interior and exterior surfaces of a user's upper and lower dentitions, respectively, the upper and lower generally arched-shaped members comprising an identical moldable, biocompatible polymeric material;

the lower generally arch-shaped member comprising lower right and lower left generally arch-shaped eyeteeth extensions of the same moldable, biocompatible polymeric material formed integrally therewith, transitioning smoothly to a flat generally horizontal molar area adjacent left and right lower molar areas, and the upper generally arch-shaped member comprising upper right and upper left molar extensions of the same moldable, biocompatible polymeric material formed integrally therewith, the upper molar extensions projecting generally perpendicularly away from the upper generally arch-shaped member and generally toward a flat generally horizontal molar area adjacent left and right lower molar areas of the lower generally arch-shaped member;

the molar extensions and generally arch-shaped eyeteeth extensions configured such that when the user bites, the molar extensions impinge on the eyeteeth extensions at respective left and right elongate, continuous, non-undulating, forward-inclined ramps extending from a right posterior position to each respective arch, the right and left forward-inclined ramps each angled at a substantially equal non-zero ramp angle to a plane defined by the mandible;

the molar extensions, eyeteeth extensions, and ramp angle further configured such that, when the apparatus is in a user's mouth, the lower dentition, the lower generally arched-shaped member, and mandible are not constrained in forward movement, and allow the lower generally arch-shaped member, lower dentition and mandible to move downward when moved back toward the user's throat, tending to keep a user's throat airway open; and the upper and lower generally arch-shaped members, and anterior surfaces of the generally arch-shaped lower eyeteeth extensions, configured to form a gap sufficient for at least a portion of the user's tongue to extend forward into the gap without being impeded in forward movement by the apparatus.

In certain embodiments, the moldable, biocompatible polymeric material is selected from the group consisting of synthetic and natural materials. In certain apparatus the moldable, biocompatible polymeric material is selected from the group consisting of polyurethanes, polysulfones, polycarboxylates, perfluorinated polymers, polyacrylics, polyvinyls, polyvinyl alcohols, silicones, polyolefins, and blends and copolymers thereof. In certain apparatus the moldable, biocompatible polymeric material is selected from a durable fade-resistant acrylic that retains its shape and color for at least four years, and a very pliable, soft, custom-injected silicone.

In certain embodiments, the upper and lower generally arched-shaped members each consist essentially of an identical moldable, biocompatible polymeric material. In certain embodiments, one or more of the molar extensions may have a magnet embedded therein, for example, non-attracting magnets in opposing molar extensions that repel and gently overcome the tendency of the user to close the jaws. Any of the apparatus described herein may be part of a kit comprising one or both upper and lower generally arch-shaped members substantially as described herein, in certain embodiments packaged in a carrying case.

Further aspects and advantages of apparatus and methods of the present disclosure will become apparent by reviewing the detailed description that follows.

Figure 1:
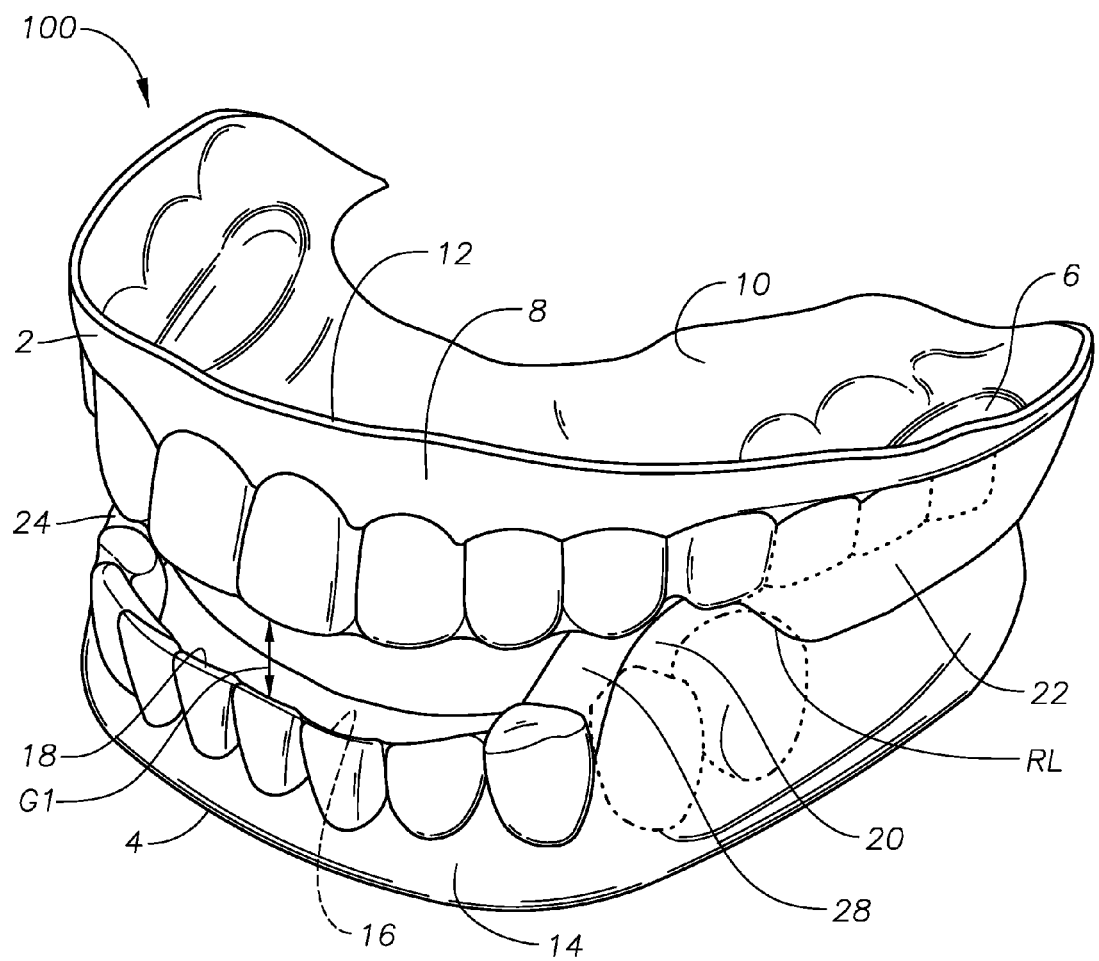
FIGS. 1 and 3 are perspective views.

It is to be noted, however, that the appended drawings are not to scale and illustrate only typical embodiments of this disclosure, and are therefore not to be considered limiting of its scope, for the apparatus, kits, and methods of the disclosure may admit to other equally effective embodiments. Identical reference numerals are used throughout the several views for like or similar elements.

DETAILED DESCRIPTION

In the following description, numerous details are set forth to provide an understanding of the disclosed oral devices, kits and methods of their use. However, it will be understood by those skilled in the art that the oral devices, kits, and methods covered by the claims may be practiced without these details and that numerous variations or modifications from the specifically described embodiments may be possible and are deemed within the claims. All U.S. published patent applications and U.S. Patents referenced herein are hereby explicitly incorporated herein by reference. In the event definitions of terms in the referenced patents and applications conflict with how those terms are defined in the present application, the definitions for those terms that are provided in the present application shall be deemed controlling.

As used herein the phrase "generally arched-shaped" means the shape of a member resembles an arch in the same way that the upper and lower teeth of a user resemble arches. The phrase "adjacent at least a portion of interior and exterior surfaces", as that term is used herein when referring to the "upper and lower generally arched-shaped members configured to fit adjacent at least a portion of interior and exterior surfaces of a user's upper and lower dentitions", means that these members are adjacent to and touching at least one surface of the upper or lower teeth concerned, but some "looseness" is allowed, so that the members may move away from the teeth slightly, for example if the material of the member stretches or deforms, such as during insertion into or removal from the mouth. The terms "eyeteeth extension" and "molar extension" are meant to convey general location, and do not mean that the extensions are always precisely covering eyeteeth or all molars in those locations; in other words, a they are meant to be relative terms, such as front and back, upper and lower, and the like, are relative terms. "Eyeteeth" or "eyetooth" location is generally between lower (mandibular) molars and lower incisors; "molar" is generally upper molar, although lower molar areas may have slight extensions. As used herein the term "user" means a human or other mammal that employs an apparatus of this disclosure in its mouth. The term "subject" may also be used and is considered interchangeable with the term "user." As used herein the term "non-undulating" means lacking any feature or features that would tend to immobilize the mandible with respect to the upper jaw, and/or that might accumulate food particles, including, but not limited to, surface roughness, fasteners such as adhesives and hook and loop fasteners, and shapes such as saw tooth steps.

The present disclosure relates generally to apparatus, kits, and methods for reducing or eliminating sleep and other disorders, and more specifically to apparatus for reducing or eliminating obstructive sleep apnea (OSA), snoring, and/or nasal drainage. A particular use for apparatus and kits of this disclosure is for humans, but they may also be used for other mammals. Certain embodiments may also be used as athletic mouth guards for upper, lower, or both dentitions.

In certain embodiments, the gap (denoted G1 in the various figures) may have a distance ranging from about 1 to about 20 mm, or from about 5 to about 15 mm.

The lateral length of the upper and lower molar extensions, i.e., the distance from the posterior terminus to the anterior terminus of a given molar extension, may be 10 mm or more, or may range from 10 to about 50 mm or from about 12 to about 24 mm.

In certain embodiments the lower, generally arch-shaped eyeteeth extensions may have a vertical height of 20 mm or less (in certain embodiments 16 mm or less, in certain embodiments 10 mm or less) at their anterior terminus, decreasing toward the posterior terminus, as illustrated herein in the various figures. The lower, generally arch-shaped eyeteeth extensions essentially comprise the entire vertical length at the anterior terminus, while the upper molar extensions essentially comprise the entire vertical length at the posterior terminus.

In certain embodiments the upper and lower members each may comprise a moldable material selected from the group consisting of synthetic and natural materials. Synthetic materials may be selected from the group consisting of polymeric materials, as further discussed herein. In certain apparatus the arch-shaped members and the molar extensions comprise a polymeric material.

Figure 4:
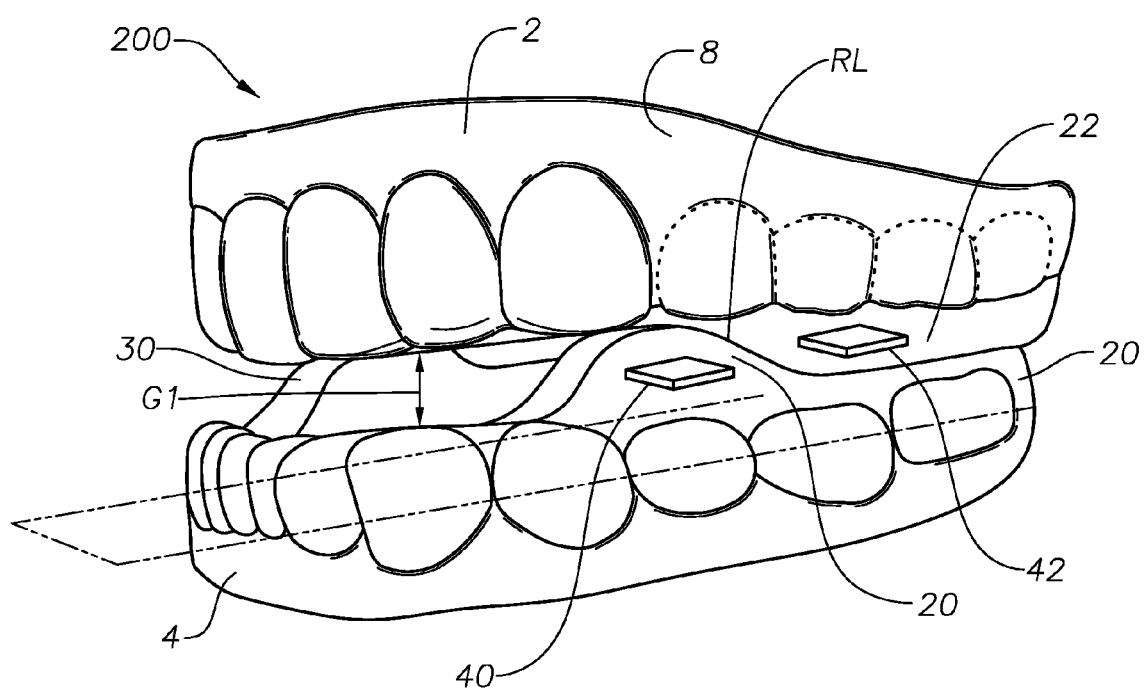
FIG. 4 is a perspective view of another apparatus or kit embodiment within the present disclosure.

In certain embodiments, the molar extensions and eyeteeth extensions may comprise at least one magnet. In certain embodiments the magnets are embedded in the polymeric material of the molar and eyeteeth extensions. In certain embodiments, an upper right magnet has polarity opposite that of a lower right magnet, and an upper left magnet has a polarity opposite that of a lower left magnet. In certain embodiments, the magnets may be flat shaped and embedded into the plastic of the molar and eyeteeth extensions. In certain embodiments, such as illustrated in FIG. 4, the flat-shaped magnets may have a north pole on one of their major surfaces and a south pole on its other major surface.

Figure 2:
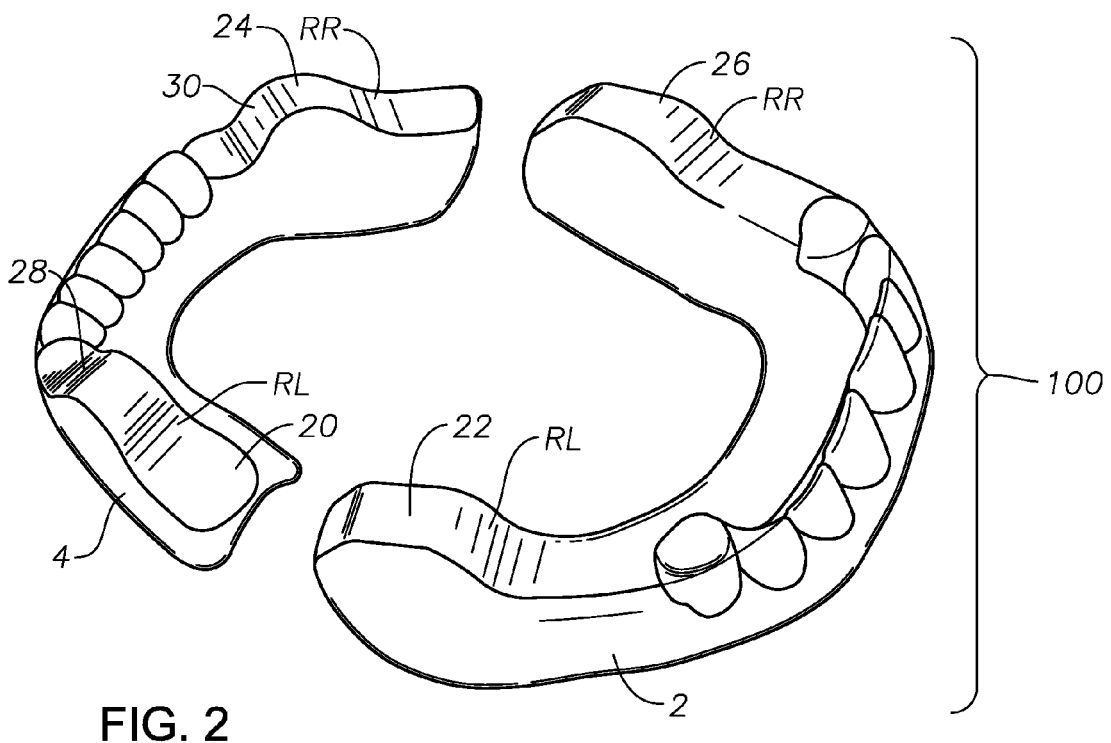
FIG. 2 is an exploded perspective view, of one apparatus or kit embodiment within the present disclosure.
Figure 3:
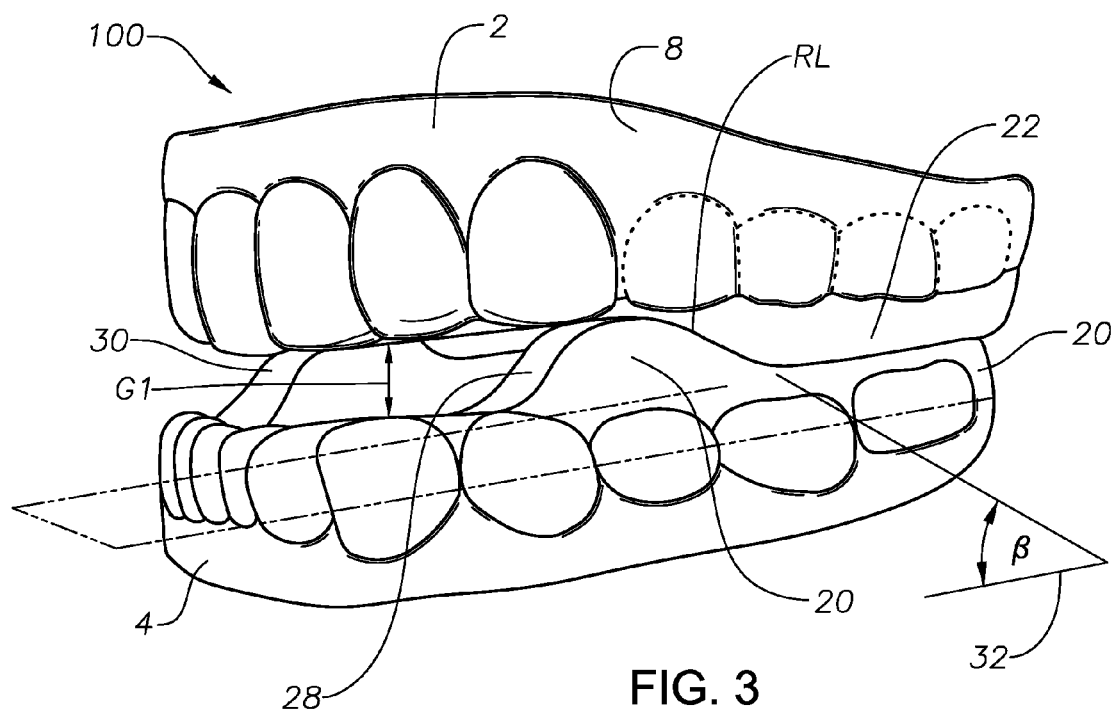

Referring now to FIGS. 1, 2, and 3 there is illustrated schematically a perspective view of one apparatus 100 in accordance with the disclosure. Apparatus embodiment 100 includes an upper generally arch-shaped member 2 and a lower generally arch-shaped member 4. Upper generally arch-shaped member 2 includes an exterior wall 8 and an interior wall 10, custom-shaped for the user's upper dentition, and which together define a trough 6 for friction fitting adjacent the upper dentition of a user. An upper connecting portion 12 connects exterior wall 8 and interior wall 10. Connecting portion 12 may be rather thin or pointed in the area of the front teeth, and rather flat or planar in the area of the back molar teeth. Similarly, lower generally arch-shaped member 4 includes an exterior wall 14, and an interior wall 16. A lower connecting portion 18 connects walls 14 and 16, and as with upper connecting portion 12, lower connecting portion 18 may be rather thin or pointed near the front teeth of the user, and rather flat or planar near the lower molars of the user.

Embodiment 100 includes a lower left, generally arch-shaped eye tooth extension 20 and an upper left molar extension 22, each extending generally perpendicularly away from their respective members. FIG. 2 illustrates schematically upper generally arch-shaped member 2 in a 180 degree flip from its "in use" position to more clearly illustrate a lower right, generally arch-shaped eye tooth extension 24 and an upper right molar extension 26. Members 2 and 4, as well as extensions 20, 22, 24, and 26 may comprise the same moldable polymeric material. Lower generally arch-shaped member 4 may comprise, or consist essentially of, or consist of lower left and lower right generally arch-shaped eyeteeth extensions (20, 24) of the same moldable, biocompatible polymeric material formed integrally therewith. Upper generally arch-shaped member 2 may comprise, or consist essentially of, or consist of upper left and upper right molar extensions (22, 26) of the same moldable, biocompatible polymeric material formed integrally therewith. Upper molar extensions 22, 26 project generally perpendicularly away from upper generally arch-shaped member 2 and generally toward respective lower molar regions of member 4 in mating configuration.

FIGS. 1-3 illustrate schematically an offset or ramp R between upper portion 2 and lower portion 4 created by a left ramp area (RL) and a right ramp area (RR). Extensions 20, 22, 24, and 26 are configured such that when the user bites, upper right molar extension 26 impinges on lower right eye tooth extension 24 at an elongate, continuous, non-undulating, forward-inclined right ramp RR extending from a right posterior position to a right anterior position 30, and upper left molar extension 22 impinges on lower left eye tooth extension 20 at an elongate, continuous, non-undulating, forward-inclined left ramp RL extending from a left posterior position to a left anterior position 28, the right and left forward-inclined ramps RR, RL each angled at a substantially equal non-zero ramp angle β to a plane 32 roughly defined by the mandible of the user (FIG. 3). In certain embodiments the ramp angle may range from about 5 to about 35 degrees, or from about 10 to about 25 degrees.

Extensions 20, 22, 24, and 26 and ramp angle β are selected and configured such that, when the apparatus is in a user's mouth, the lower dentition, lower generally arched-shaped member 4, and mandible are not constrained in forward (anterior) movement, and allow lower generally arch-shaped member 4, lower dentition and mandible to move downward when moved back (posterior) toward the user's throat, tending to keep a user's throat airway open. Furthermore, upper and lower generally arch-shaped members 2, 4, and anterior surfaces 28, 30 of lower, generally arch-shaped eyeteeth extensions 20, 24, are configured to form a gap G1 sufficient for at least a portion of the user's tongue to extend forward into the gap without being impeded in forward movement by the apparatus, and without the tongue being constrained, pulled or grabbed in any way.

During use, lower left generally arch-shaped eye tooth extension 20 may slidingly move adjacent matching tapered upper left molar extension 22 in the area of left ramp area RL (FIGS. 1 and 3), where faces of extensions 20 and 22 may slide against each other at ramp angle β. Similarly on the right side, lower right generally arch-shaped eye tooth extension 24 may slidingly move adjacent matching tapered upper right molar extension 26 (not viewable in FIGS. 1 and 3, but illustrated in exploded view of FIG. 2). Ramps RL and RR allow free and unlimited forward movement of the lower dentition, the lower generally arched-shaped member 4, and mandible and create a tendency for the lower generally arch-shaped member 4, lower dentition and mandible to move downward as they move back toward the user's throat. Movement of the lower jaw backwards is a natural movement during sleep. As this occurs, embodiment 100 will tend to keep the airway open by creating a gap between upper portion 2 and lower portion 4, near the front teeth, as indicated by double-headed arrow G1 in FIGS. 1 and 3, and partially defined by space between anterior portions of lower extensions 20, 24. This gap may be important in methods of reducing nasal drainage, perhaps more important than forward movement of the lower jaw.

FIG. 4 is a perspective view of another apparatus or kit embodiment 200 within the present disclosure. As generally may be seen in FIG. 4, magnets 40 and 42 have, in this embodiment, a specific spatial relationship. The respective north and south poles of these magnets are arranged so that when placed as viewed in FIG. 4, they will substantially repel one another by virtue of their respective magnetic field lines being unable to cross, forcing the mandible down if it should move posteriorly, for example naturally during sleep, or otherwise. Other magnets may be present, arranged similarly with the same spatial and magnetic relationship, in lower and upper right extensions 24, 26. As this occurs, embodiment 200 will tend to keep a user's airway open by creating a gap between upper portion 2 and lower portion 4, near the front teeth, as indicated by double-headed arrow G1 in FIG. 3 through action of ramps RR and RL combined with repelling action of the magnets. Note that the magnetic poles of each magnet could be reversed to arrive at substantially the same embodiment. In both embodiment 200 and its "reverse" poles sister embodiment, there will be magnetic repulsion between magnets 40, 42, as well as between similar magnets on right side. In certain embodiments, repelling magnets may only be required on the left or the right, depending on the muscular strength of the user's jaw muscles. In this embodiment and others like it, the magnetic attraction and repulsion thus may be adjusted depending on the particular user, for example the strength of the user's jaw muscles.

The materials of construction of the upper and lower general arch-shaped members and integral extensions may comprise any moldable plastic (polymeric) material that is approved for use in oral medical devices and appliances for human use and that may be custom fitted for each user and tooth-retained via friction grip, and materials approved for animal use. The members may comprise a single material, or combination of materials. The members may comprise more than one layer of material, and each layer may be the same or different. The polymeric materials may be filled with various fillers, extenders, pigments, and other additives. In embodiments consisting essentially of moldable, biocompatible polymeric material, these fillers, extenders, pigments, and other additives are present in limited amounts to the extent necessary to substantially exceed minimum safety and effectiveness standards. Suitable polymeric materials include thermoplastics, thermosetting polymers, elastomers, and thermoplastic elastomers. The polymeric materials may comprise co-polymers, ter-polymers, and blends of two or more chemical types of polymers, or blends of two or more polymers of the same chemical type, for example, a blend of two thermoplastics having different molecular weights.

Examples of specific polymers include polyacrylics, polyvinyls, polyvinyl alcohols, and the like. An example of a suitable polymeric material is a durable fade-proof acrylic that retains its shape and color for at least four-five years. Another example is made of a very pliable, soft, custom-injected silicone. Another example is a polymeric material compatible with home/office based bleaching techniques, such as the material used to make an OSAP device, and materials that can be molded into a ready-made semi-universal trial version, which may be suitable for patients who cannot endure having their impressions taken. In addition, the trial version is an inexpensive way to test a particular patients' tolerance to oral therapy. Another example is the material used in the device known under the trade designation SAGA. This device consists of a hard acrylic shell laminated to a soft vinyl liner. Another example is the acrylic material (Bruxeze™) that softens in hot water to provide a combination of comfort, strength, and retention, and which is used in the Adjustable PM Positioner™, an appliance that fits over all maxillary and mandibular teeth. Another example are the materials used in the device known as SomnoGuard® AP, which consists of an upper and a lower tray each made of two materials. The outer tray shells consist of solid clear and transparent medical grade polycarbonate. The inner lining which accommodates the teeth impressions is made of a thermoplastic copolymer. After the oral appliance is heated in a hot water bath its thermoplastic body molds easily to the teeth and jaws allowing any medical doctor to fit the device chair side. Yet another example is the material employed in the device known as SomnoGuard AP Pro®, which is a dental lab made two-part mandibular adjustable positioner to treat snoring and mild to moderate sleep apnea, and comprises common acrylic/elastomeric thermoform dental materials available in any dental lab after taking impressions of the lower and upper jaws and producing plaster models. Other polymeric materials that may be useful include nitinol, silicone, a PET, or any other biocompatible polymeric material. Other possible examples include PTFE, e-PTFE, polypropylene, polyurethane, polycarbonate, polyethylene terephthalate, stainless steel, titanium, tantalum, gold, polyvinidylene fluoride and combinations thereof "Biocompatibility" may be determined in accordance with national and/or international standards, such as ISO 10993.

The molar and eyeteeth extensions are integrally molded with their respective upper or lower generally arch-shaped members as illustrated schematically in FIGS. 1-4 using special molds. In order to achieve better fit, for example between ramps, the ramps may be built up by applying a paste or solution of polymeric precursor materials and swabbing the precursors materials on the appropriate areas. In certain embodiments, this may need to be done repeatedly to build up the molar extension to functional length.

Magnets which may be useful in apparatus of this disclosure include rare earth magnets, such as samarium-cobalt and neodymium-iron-boron magnets. It has become possible to produce magnets with small enough dimensions for dental applications and yet still provide the necessary forces. Certain embodiments may employ magnets of the "closed field" type. In this type of system, a soft magnetic or ferromagnetic material, such as ferritic or martensitic stainless steel or Pd—Co—Ni alloy, is implanted into the jaw, rather than a magnet, to provide attractive force to hold the denture in place. This implant is known as a "keeper". In this configuration, the magnetic field lines are shunted through the keeper as it is the path of minimum energy and there is no magnetic field experienced in the oral cavity. U.S. Pat. Nos. 6,659,771, 5,678,998, 5,013,243 and 6,299,450 describe small yet powerful magnets for cooperating with a non-magnet implanted "keeper" for denture attachment. The non-magnet keeper is made of a magnet-attracted material, such as a soft magnetic or ferromagnetic material, but is not a permanent magnet. U.S. Pat. No. 4,396,373 describes a removable orthodontic appliance having two permanent magnets carried by two caps, respectively, having facing poles which are in registry when the mouth is normally closed, exerting a magnetic force in a direction substantially normal to the occlusal plane. The opposing magnets have confronting poles with like-polarity such that the magnets repel and develop intrusive forces upon the respective teeth. U.S. Pat. No. 4,671,767 discloses both fixed and removable orthodontic devices that use magnets. The magnets are secured to removable or fixed orthodontic devices and are positioned bilaterally in the posterior molar regions. The faces of the magnets are oriented such that they repel each other, thereby creating magnetic forces parallel to the occlusal plane for urging the mandible forward.

According to U.S. Pat. No. 7,712,468, which discloses a removable magnetic dental appliance, the magnetic orthodontic devices described above employ "open field" magnetic configurations, which are potentially harmful to the local tissues in the oral cavity, especially since the devices are designed for long-term use. Furthermore, the appliances are uncomfortable to wear.

Any of the magnets discussed in these patent and publications would be useable in apparatus and kits disclosed herein.

Although the foregoing description is intended to be representative of apparatus, kits, and methods in accordance with the present disclosure, it is not intended to in any way limit the scope of the appended claims.

What is claimed is:
1. An apparatus comprising:
upper and lower generally arched-shaped members configured to fit adjacent at least a portion of interior and exterior surfaces of a user's upper and lower dentitions, respectively, the upper and lower generally arched- shaped members comprising an identical moldable, biocompatible polymeric material;

the lower generally arch-shaped member comprising lower right and lower left anterior generally arch-shaped eyeteeth extensions of the moldable, biocompatible polymeric material formed integrally therewith, transitioning smoothly to a posterior flat generally horizontal molar area adjacent left and right lower molar areas, and the upper generally arch-shaped member comprising upper right and upper left posterior molar extensions of the moldable, biocompatible polymeric material formed integrally therewith, the upper molar extensions projecting generally perpendicularly away from the upper generally arch-shaped member and generally toward the posterior flat generally horizontal molar area adjacent left and right lower molar areas of the lower generally arch-shaped member;

the upper right and upper left posterior molar extensions and lower right and lower left generally arch-shaped eyeteeth extensions configured such that when the user bites, the upper right and upper left posterior molar extensions impinge on the lower right and lower left generally arch-shaped eyeteeth extensions at respective left and right elongate, continuous, non-undulating, forward-inclined ramps extending from a posterior position to each respective generally arch-shaped eyeteeth extension, the right and left elongate, continuous, non-undulating, forward-inclined ramps each angled at a substantially equal non-zero ramp angle to a plane defined by a mandible;

the upper right and upper left posterior molar extensions, eyeteeth extensions, and ramp angle further configured such that, when the apparatus is in a user's mouth, a lower dentition, the lower generally arched-shaped member, and mandible are not constrained in forward movement, and allow the lower generally arch-shaped member, lower dentition and mandible to move downward when moved back toward the user's throat, tending to keep a user's throat airway open; and the upper and lower generally arch-shaped members, and anterior surfaces of the generally arch-shaped lower eyeteeth extensions, configured to form a gap sufficient for at least a portion of the user's tongue to extend forward into the gap without being impeded in forward movement by the apparatus;

wherein the upper right and upper left posterior molar extensions and eye teeth extensions comprise at least one magnet.

2. The apparatus of claim 1 wherein the moldable, biocompatible polymeric material is selected from the group consisting of synthetic and natural materials.

3. The apparatus of claim 2 wherein the moldable, biocompatible polymeric material is selected from the group consisting of polyurethanes, polysulfones, polycarboxylates, perfluorinated polymers, polyacrylics, polyvinyls, polyvinyl alcohols, silicones, polyolefins, and blends and copolymers thereof.

4. The apparatus of claim 3 wherein moldable, biocompatible polymeric material is selected from a durable fade-resistant acrylic that retains its shape and color for at least four years, and a very pliable, soft, custom-injected silicone.

* * * * *